United States Patent
Hancu et al.

(10) Patent No.: US 7,557,058 B2
(45) Date of Patent: Jul. 7, 2009

(54) CATALYST COMPOSITION AND METHOD FOR CHLORINATING AROMATIC COMPOUNDS

(75) Inventors: Dan Hancu, Clifton Park, NY (US); Robert Edgar Colborn, Niskayuna, NY (US); Richard Joseph Kilmer, Charlton, NY (US)

(73) Assignee: Sabic Innovative Plastics IP B.V. (NL)

( * ) Notice: Subject to any disclaimer, the term of this patent is extended or adjusted under 35 U.S.C. 154(b) by 0 days.

(21) Appl. No.: 11/305,906

(22) Filed: Dec. 19, 2005

(65) Prior Publication Data
US 2006/0094912 A1    May 4, 2006

Related U.S. Application Data

(62) Division of application No. 10/391,370, filed on Mar. 18, 2003, now Pat. No. 7,012,166.

(51) Int. Cl.
*B01J 31/00* (2006.01)

(52) U.S. Cl. .................. 502/150; 502/155; 502/168
(58) Field of Classification Search .......... 502/165, 502/168, 170, 171, 150, 155
See application file for complete search history.

(56) References Cited

U.S. PATENT DOCUMENTS

| | | | |
|---|---|---|---|
| 3,226,447 A | 12/1965 | Bing et al. | |
| 4,017,551 A | 4/1977 | Milam et al. | |
| 4,031,142 A | 6/1977 | Graham | |
| 4,031,147 A | 6/1977 | Graham | |
| 4,069,264 A * | 1/1978 | Lin | 570/209 |
| 4,190,609 A | 2/1980 | Lin | |
| 4,250,122 A | 2/1981 | Lin et al. | |
| 4,289,916 A | 9/1981 | Nakayama et al. | |
| 4,647,709 A | 3/1987 | Wolfram | |
| 4,925,994 A | 5/1990 | Mais et al. | |
| 5,621,153 A * | 4/1997 | Krishnamurti et al. | 570/209 |
| 5,714,603 A * | 2/1998 | Krishnamurti et al. | 540/455 |
| 2001/0021788 A1* | 9/2001 | Matsumoto et al. | 562/532 |

FOREIGN PATENT DOCUMENTS

| | | |
|---|---|---|
| EP | 0 126 669 | 11/1984 |
| SU | 654602 | 10/1976 |

* cited by examiner

*Primary Examiner*—Michael A Marcheschi
*Assistant Examiner*—James E McDonough
(74) *Attorney, Agent, or Firm*—Cantor Colburn LLP

(57) ABSTRACT

The present invention provides a catalyst composition prepared by combining (A) at least one salt and (B) at least one organic sulfur compound. The salt includes a metal cation of a metal selected from the group consisting of copper, nickel, cobalt, manganese, molybdenum, zirconium, titanium, vanadium, niobium, palladium, and platinum and an organic counterion to the metal cation, derived from at least one acidic organic compound selected from the group consisting of those with an approximate pKa value relative to water of at least about 3. The catalyst compositions provided by the invention are useful for the selective chlorination of aromatic compounds such as toluene and o-xylene.

28 Claims, No Drawings

CATALYST COMPOSITION AND METHOD FOR CHLORINATING AROMATIC COMPOUNDS

This application is a divisional of application Ser. No. 10/391,370 (now U.S. Pat. No. 7,012,166) filed Mar. 18, 2003.

BACKGROUND OF THE INVENTION

This invention relates to the chlorination of aromatic compounds. More particularly, it relates to chlorination methods and catalyst compositions capable of producing predominantly p-chloro isomers.

Chlorination of such aromatic compounds as toluene and xylenes is a known reaction affording useful compounds. The most useful of these compounds for many purposes are the p-chloro compounds. p-Chlorotoluene, for example, is an intermediate capable of conversion into many useful chemicals. The same is true of p-chloro-o-xylene; i.e., 4-chloro-1,2-dimethylbenzene. A principal utility of the latter compound is its conversion by oxidation to 4-chlorophthalic acid, which is in turn an important intermediate in the production of polyetherimides.

However, the production of these highly desirable chlorinated compounds is complicated by the simultaneous production of numerous not so desirable by-products. Thus, chlorination of toluene and xylenes produces the p-monochloro isomer in admixture with other isomers such as o-chlorotoluene and 3-chloro-1,2-dimethylbenzene. In addition, numerous polychlorinated products are ordinarily obtained.

Many of the known methods for chlorination of aromatic compounds employ elemental chlorine in combination with Lewis acids, chiefly the Lewis acids known in the art as useful in Friedel-Crafts reactions including alkylation and acylation. The use of such catalytic species as ferric chloride, antimony trichloride, antimony pentachloride, zinc chloride and aluminum chloride is conventional.

However, the use of such catalysts in no way resolves the problems of isomer distribution and polychlorination. Various publications, including many U.S. patents, go further in describing mixed catalyst systems in which another catalyst component is an organosulfur compound. The organosulfur compounds disclosed in these publications are of very diverse structures. Many of them are phenoxathiins or thianthrenes. Illustrative patents with such disclosures are U.S. Pat. Nos. 3,226,447, 4,031,142, 4,031,147, 4,190,609, 4,250,122, 4,289,916, 4,647,709 and 4,925,994. Lewis acid proportions employed according to many of these disclosures are quite low, typically on the order of 0.01% by weight based on aromatic compound being chlorinated.

U.S. Pat. No. 4,017,551 discloses the chlorination of benzene or monochlorobenzene in the presence of iron-free manganese chloride. No second catalyst component is disclosed.

In European patent application 126,669, a further class of catalyst systems is disclosed. It comprises a Lewis acid known to be useful for this purpose, preferably a chloride of iron or antimony, in combination with an N-substituted phenothiazine. Among the substituted phenothiazines disclosed is phenothiazine N-carbonyl chloride. It has been found, however, that such combinations are still somewhat deficient in that they tend to form polychloro compounds and monochloro compounds other than the p-isomer.

Soviet patent 654,602 discloses the chlorination of toluene in the presence of a chloride of copper, cobalt or nickel on a solid support. The chlorination requires vapor phase conditions and temperatures in the range of 400-450° C. Such conditions are far from ideal for commercial practice.

SUMMARY OF THE INVENTION

The present invention provides methods and catalyst compositions for formation primarily of a p-monochlorinated aromatic compound, using relatively mild conditions easily achieved in a commercial operation.

In one embodiment the invention is a method for chlorinating an aromatic compound which comprises contacting said aromatic compound with chlorine in the presence of a catalyst combination prepared by combining (A) at least one salt comprising a metal selected from the group consisting of a Group 4-12 metal, lanthanides and actinides; and an organic counterion derived from at least one acidic organic compound selected from the group consisting of those with an approximate pKa value relative to water of at least about 3; and (B) at least one organic sulfur compound. In another embodiment the invention is a method for chlorinating toluene or o-xylene which comprises contacting said toluene or o-xylene with chlorine in the presence of a catalyst combination prepared by combining (A) at least one salt of copper, nickel, cobalt or manganese with a carboxylic acid or 2,4-dione, or derivative thereof; and (B) at least one organic sulfur compound selected from the group consisting of phenothiazine-N-carbonyl chloride, N-trifluoroacetylphenothiazine, 3-chloro-N-trifluoroacetylphenothiazine or 3-trifluoromethyl-N-trifluoroacetylphenothiazine. In another embodiment the invention is a method for chlorinating toluene or o-xylene which comprises contacting said toluene or o-xylene with chlorine in the presence of a catalyst combination prepared by combining (A) copper sulfate; and (B) at least one organic sulfur compound. In another embodiment the invention is a method for chlorinating an aromatic compound which comprises contacting said aromatic compound with chlorine in the presence of a catalyst combination comprising (1) (A) at least one salt comprising a metal selected from the group consisting of a Group 4-12 metal, lanthanides and actinides; and an organic counterion derived from at least one acidic organic compound selected from the group consisting of those with an approximate pKa value relative to water of at least about 3; and (B) at least one organic sulfur compound, or (2) a reaction product comprising (A) and (B), or (3) the components (A), (B) and a reaction product comprising at least one of (A) or (B). In another embodiment the invention is a catalyst composition prepared by combining (A) at least one salt comprising a metal selected from the group consisting of a Group 4-12 metal, lanthanides and actinides; and an organic counterion derived from at least one acidic organic compound selected from the group consisting of those with an approximate pKa value relative to water of at least about 3; and (B) at least one organic sulfur compound. In another embodiment the invention is a catalyst composition for chlorinating toluene or o-xylene which comprises at least one reaction product of (A) at least one salt comprising a metal selected from the group consisting of a Group 4-12 metal, lanthanides and actinides; and an organic counterion derived from at least one acidic organic compound selected from the group consisting of those with an approximate pKa value relative to water of at least about 3; and (B) at least one organic sulfur compound. In another embodiment the invention is a catalyst composition for chlorinating toluene or o-xylene which comprises (A) at least one salt of copper, nickel, cobalt or manganese with a carboxylic acid or 2,4-dione, or derivative thereof; and (B) at least one organic sulfur compound selected from the group consisting of phenothiazine-N-carbonyl chloride, N-trifluoroacetylphenothiazine, 3-chloro-N-trifluoroacetylphenothiazine or 3-trifluoromethyl-N-trifluoroacetylphenothiazine. In another embodiment the invention is a catalyst composition for chlorinating toluene or o-xylene which comprises at least one reaction product of (A) at least one salt of copper, nickel, cobalt or manganese with a carboxylic acid or 2,4-dione, or derivative thereof; and (B) at least one organic sulfur compound selected from the group consisting of phenothiazine-N-carbonyl chloride, N-trifluoroacetylphenothiazine, 3-chloro-N-trifluoroacetylphenothiazine or 3-trifluoromethyl-N-trifluoroacetylphenothiazine. In another embodiment the invention is a catalyst composition prepared by combining (A) copper sulfate; and (B) at least one organic sulfur compound. In another embodiment the invention is a catalyst composition for chlorinating toluene or o-xylene which comprises (A) copper sulfate; and (B) at least one organic sulfur compound selected from the group consisting of phenothiazine-N-carbonyl chloride, N-trifluoroacetylphenothiazine, 3-chloro-N-trifluoroacetylphenothiazine or 3-trifluoromethyl-N-trifluoroacetylphenothiazine. In still another embodiment the invention is a catalyst composition for chlorinating toluene or o-xylene which comprises at least one reaction product of (A) copper sulfate; and (B) at least one organic sulfur compound selected from the group consisting of phenothiazine-N-carbonyl chloride, N-trifluoroacetylphenothiazine, 3-chloro-N-trifluoroacetylphenothiazine or 3-trifluoromethyl-N-trifluoroacetylphenothiazine. Various other features, aspects, and advantages of the present invention will become more apparent with reference to the following description and appended claims.

DETAILED DESCRIPTION; PREFERRED EMBODIMENTS

Any aromatic compound may be chlorinated by the method of this invention. Included are monocyclic and polycyclic hydrocarbons and substituted derivatives thereof. For the most part, the chlorination of monocyclic aromatic hydrocarbons is contemplated. Such hydrocarbons include benzene, toluene, o-, m- and p-xylene and 1,2,4,5-tetramethylbenzene. It is preferred that the aromatic hydrocarbon contain at least one $C_{1-4}$ alkyl substituent, preferably methyl, and that a p-position with respect to one of the alkyl groups be free from substituents of any kind. Most preferred are toluene and o-xylene.

In an embodiment of the invention, the aromatic compound is contacted with chlorine in the presence of a catalyst combination to effect reaction. Contact may be by bubbling chlorine through the liquid aromatic compound, optionally in the presence of a suitable solvent although no solvent is ordinarily necessary. In one embodiment the reaction takes place preferably in the liquid phase rather than in the vapor phase.

For the sake of brevity, the constituents of the catalyst combination are defined as "components" irrespective of whether a reaction involving said constituents occurs before or during the chlorination reaction. Thus, the catalyst system combination may include the reaction products derived from at least one of the components. Said reaction products may comprise chlorine. Said reaction products may or may not be in admixture with one or more unreacted components remaining in the catalyst combination. Generally, the catalyst combination is obtained by combining components (A) and (B). Component A of the catalyst combination is at least one compound, most often a salt, of a metal selected from Groups 4-12, a lanthanide or an actinide of the Periodic Table of Elements. In some specific embodiments said metal is at least one member selected from the group consisting of copper, nickel, cobalt, manganese, molybdenum, zirconium, titanium, vanadium, niobium, palladium or platinum. Said salt may be of an inorganic acid; illustrative salts of this type are cupric sulfate, nickel chloride, cobalt (III) chloride and manganese (II) chloride. Preferably, however, the salt is one which is at least somewhat soluble in the reaction medium. Included in this subcategory are salts wherein the anion is derived from an acidic organic compound, said salt having at least some solubility in a hydrophobic, organic solvent. Illustrative examples of such acidic organic compounds include, but are not limited to, those with an approximate pKa value relative to water in one embodiment of at least about 3, in another embodiment of at least about 4, in another embodiment of at least about 5, in another embodiment of at least about 6, in another embodiment of at least about 7, in another embodiment of at least about 8, and in still another embodiment of at least about 9. In some embodiments said anion is derived from a carboxylic acid or 2,4-dione, or a derivative thereof. By "2,4-dione" is meant a dicarbonyl compound, including, but not limited to, a diketone or a beta-ketoester in which a carbon atom separates the two carbonyl groups, irrespective of the placement of said carbonyl groups in the molecule. Illustrative examples of derivatives of carboxylic acids or 2,4-diones include halogenated derivatives and particularly chlorinated or fluorinated derivatives. Examples of salts suitable as component A include, but are not limited to, cupric acetate, cupric 2,4-pentanedionate, cupric 1,1,1,5,5,5-hexafluoro-2,4-pentanedionate, cupric benzoate, nickel acetate, nickel 2,4-pentanedionate, nickel 2,2,6,6-tetramethyl-3,5-heptanedionate, cobalt (II) acetate, cobalt (II) stearate, cobalt (II) 2,4-pentanedionate, manganese (II) acetate, manganese (II) stearate and manganese (II) 2,4-pentanedionate. Copper salts are usually preferred. Combinations of various salts are also useful.

Component B is at least one organic sulfur compound. Suitable compounds include dialkyl and diaryl sulfides, dialkyl and diaryl disulfides, alkyl and aryl mercaptans, phenoxathiin, thiophene, dibenzothiophene, thianthrene and phenothiazine, including substituted derivatives thereof. Component B may also be a mixture of organic sulfur compounds.

A particularly preferred sulfur compound is phenothiazine-N-carbonyl chloride, having the formula

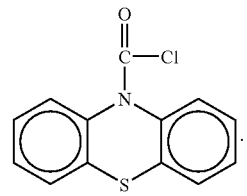

It may be synthesized by known methods such as the reaction of phenothiazine with phosgene. Also particularly effective is N-trifluoroacetylphenothiazine. Aromatically substituted analogs of the above, especially chlorinated analogs such as 2-chloro-N-trifluoroacetylphenothiazine and 2-trifluoromethyl-N-trifluoroacetylphenothiazine, are also effective.

The method of the invention may be performed by simply contacting a mixture of the aromatic compound, component A and component B with chlorine, preferably in the liquid phase, most often at a temperature in the range of about 0-100° C., preferably about 5-50° C. and most preferably below 25° C. Preferably, the reaction mixture is protected from air by contact with an inert gas such as nitrogen or argon, and is shielded from exposure to ambient light to minimize chlorination of any alkyl side chains on the aromatic compound. The term "light" in this context means radiation in the visible and ultraviolet regions of the spectrum.

On a preparative scale, contact is preferably accomplished by passing at least a portion, and more preferably substantially all, the chlorine through the mixture; however, for screening purposes it is often convenient to charge the chlorine to the head space of the reaction system, removing by-product HCl by applying a slight vacuum. Pressure may vary from said slight vacuum to superatmospheric, typically up to about 10 atm although superatmospheric pressure is generally not necessary. It is also within the scope of the invention to generate chlorine in situ from a reagent such as thionyl chloride.

On a preparative scale, chlorine can simply be passed into the mixture with periodic sampling until the desired or maximum amount of the desired p-monochloro product has been produced, as determined by art-recognized analytical methods; for example, by gas chromatography. Reactions may employ an excess, typically up to about a 50% and preferably a 10-30% stoichiometric excess of chlorine.

The proportion of component A is typically in the range of about 0.005-10.0% and of component B in the range of about 0.005-10.0% by weight based on aromatic compound; preferably, these ranges are respectively about 0.01-5.0% and about 0.01-0.1%, and most preferably 0.07-3.0% and about 0.05-0.1%. For the most part, higher proportions of component A are employed than of art-recognized Lewis acid catalysts such as ferric chloride. On the other hand, the proportion of component B according to the invention is generally lower relative to component A than is true with art-recognized catalysts. The weight ratio of component A to component B is in various embodiments in a range of between about 2000:1 and 1:2000. The ratio of component A to component B is in some particular embodiments in a range of between about 2:1 and about 100:1; in other embodiments in a range of between about 3:1 and about 80:1; and in still other embodiments in a range of between about 3:1 and about 70:1.

While the present invention is not dependent in any way on theory or reaction mechanism, it is believed that these differences in proportion of metal compound are the result of different reaction mechanisms. With a relatively strong Lewis acid such as ferric chloride, it is believed that complex formation with component B minimizes the level of acid which can produce non-selective aromatic ring chlorination; said complex, on the other hand, itself promotes selective chlorination with production of the p-isomer.

The Lewis acids employed according to the present invention, by contrast, are relatively weak and their presence in relatively large proportions is not as likely to afford non-selective aromatic chlorination, although selectivity is improved by the presence of component B. At low Lewis acid levels, however, side chain chlorination predominates to yield products that are undesirable for the purposes of the invention. Moreover, it is believed that an intermediate stage of the reaction is the chlorination of component A to form a relatively non-catalytic species, necessitating the use of a relatively high concentration thereof to compensate. Thus, reaction products of the catalyst components include those reaction products with chlorine of one or more catalyst components or intermediates derived from one or more catalyst components. Given these differences in behavior of the Lewis acids employed in this invention and the stronger prior art Lewis acids, it would in no way have been predictable that the Lewis acids employed in the invention would be effective, or in what proportions.

In situations where conditions are optimized for production of the desired p-chloro isomer, it may be possible to employ the chlorination product of the method of the invention directly for further purposes, for example as a chemical intermediate, without further purification. Sometimes, however, further purification is desirable or necessary. It may be achieved by the use of one or more conventional purification techniques, including fractional distillation, fractional crystallization and preparative-scale chromatographic methods.

It is also frequently possible to recover the catalyst combination from the chlorination reaction mixture for repeated use in subsequent reactions. This may be done by removing, at least in part, all other materials, typically by distillation.

The catalyst compositions taught herein may be employed for any reaction catalyzed by (1) the combination of (A) at least one salt comprising a metal selected from the group consisting of a Group 4-12 metal, lanthanides and actinides; and an organic counterion derived from at least one acidic organic compound selected from the group consisting of those with an approximate pKa value relative to water of at least about 3; and (B) at least one organic sulfur compound, or (2) a reaction product comprising (A) and (B), or (3) the components (A), (B) and a reaction product comprising at least one of (A) or (B). Illustrative applications of said catalyst compositions include, but are not limited to, halogenation, chlorination and Friedel-Crafts reactions.

The invention is illustrated by the following examples. All percentages are by weight. Comparisons with ferric chloride as a Lewis acid are included solely for comparative purposes to show operativeness of the invention. The abbreviation "anh" means anhydrous.

The following designations of chemicals are employed:
PNCC—phenothiazine carbonyl chloride,
FPN—N-trifluoroacetylphenothiazine,
CFPN—2-chloro-N-trifluoroacetylphenothiazine,
FFPN—2-trifluoromethyl-N-trifluoroacetylphenothiazine,
DBT—2-methyldibenzothiophene,
CuFPD—copper(II) hexafluoro-2,4-pentanedionate,
CuBZ—copper(II) benzoate,
CuPBD—copper(II) 1-phenyl-1,3-butanedionate,
CoPD—cobalt (II) 2,4-pentanedionate,
CoSt—cobalt (II) stearate,
NiPD—nickel 2,4-pentanedionate,
NiTMHD—nickel 2,2,6,6-tetramethyl-3,5-heptanedionate,
MnSt—manganese (II) stearate,
MnPD—manganese (II) 2,4-pentanedionate,
acac—2,4-pentanedionate,
$F_3$acac and $F_6$acac—fluorinated 2,4-pentanedionate,
$C_6H_5$acac—phenyl-2,4-pentanedionate.

EXAMPLES 1-5

Screening runs were performed at 10° C. and atmospheric pressure in a 48-well aluminum block reactor enclosed in a light box for protection against ambient radiation. Stirred, argon-purged glass vials containing 352 mg (3.3 mmol) of xylene, various proportions of copper(II) salts (in wt. % based on xylene) and 0.02 wt. % (based on xylene) of PNCC were placed in the reactor wells. Vials were individually stirred. Chlorine (120 mole percent based on xylene) was added to the head space of each vial for 20 minutes via a polytetrafluoroethylene gas manifold, and MONEL tubes, 1.59 mm OD. Vacuum was applied to eliminate excess chlorine as well as HCl formed in the reaction. At the end of the reaction time, residual chlorine in the vials was eliminated by purging the vials with argon for 30 minutes. The composition of the reaction mixture in each vial was determined by gas chromatography.

The results are given in Table I, in comparison with Control 1 in which the copper salt was replaced by 0.01% of ferric chloride. "Conversion" is the percentage of xylene converted to chlorinated products. The abbreviation "mono-Cl" designates the amount of aromatically monochlorinated products (i.e., products in which the aromatic ring is monochlorinated as opposed to those in which the side chain is chlorinated) as a percentage of total chlorinated products, and "4-Cl" designates the amount of the 4-monochloro (p-chloro) isomer as a percentage of total aromatically monochlorinated products.

TABLE I

| Example | Lewis acid | Cu compound, wt. % | PNCC, wt. % | Conversion, % | Mono-Cl, % | 4-Cl, % |
|---|---|---|---|---|---|---|
| 1 | CuFPD | 0.37 | 0.02 | 67 | 98 | 80.8 |
| 2 | CuFPD | 1.1 | 0.02 | 82 | 96.6 | 82.6 |
| 3 | CuBZ | 1.4 | 0.02 | 75 | 97 | 80 |
| 4 | CuSO₄ (anh) | 1.4 | 0.02 | 77 | 95 | 77.3 |
| 5 | CuPBD | 1.4 | 0.02 | 82 | 96 | 77.5 |
| Control 1 | FeCl₃ | — | 0.1 | 91 | 92.7 | 74.5 |

It is evident from the results in Table I that satisfactory conversions and advantageous product distributions are obtained by the present invention. This is particularly true in Examples 1-3, employing copper salts of acidic organic compounds.

EXAMPLE 6

Xylene (6.9 g, 65 mmol), PNCC (0.1 wt. %) and CuFPD (1.5 wt. %) were charged to an argon-purged flask which was screened from ambient light. The mixture was cooled to 10° C. and flushed with argon. Chlorine was bubbled into the mixture at constant flow rate for 35 minutes, with periodic analysis by gas chromatography. Conversion, mono-Cl and 4-Cl levels at 25 minutes were 77.0%, 98.5% and 80%, respectively, and at 30 minutes 94.8%, 96%, 81%, respectively. In Control 2 employing 0.01% ferric chloride in place of the CuFPD, these values at 25 minutes were 68%, 99%, and 72%, respectively, and at 30 minutes 89%, 95.9% and 74.6% respectively.

EXAMPLES 7-15

The procedure of Examples 1-5 was repeated, substituting other phenothiazines (0.1% based on xylene) for PNCC as component B. The results are given in Table II.

TABLE II

| Example | Cu compound, identity | Cu compound, wt. % | Component B, identity | Conversion, % | Mono-Cl, % | 4-Cl, % |
|---|---|---|---|---|---|---|
| 7 | CuBZ | 1.5 | FPN | 88 | 94 | 72.8 |
| 8 | CuFPD | 0.3 | FPN | 83 | 94 | 68.5 |
| 9 | CuSO₄ (anh) | 1.5 | FPN | 77 | 95 | 67 |
| 10 | CuBZ | 1.5 | CFPN | 85 | 95 | 75 |
| 11 | CuFPD | 0.3 | CFPN | 84 | 94.5 | 75.7 |
| 12 | CuSO₄ (anh) | 1.5 | CFPN | 80 | 95 | 75 |
| 13 | CuBZ | 1.5 | FFPN | 81 | 95 | 76 |
| 14 | CuFPD | 0.3 | FFPN | 80 | 96 | 76 |
| 15 | CuSO₄ (anh) | 1.5 | FFPN | 82 | 96 | 76.5 |

EXAMPLES 16-18

The procedure of Examples 1-5 was repeated, substituting 400 mg (3.8 mmol) of toluene for the xylene and employing CuFPD as component A and various sulfur compounds as component B. The results are given in Table III, in comparison with Control 3 employing ferric chloride at 0.024%.

TABLE III

| Example | CuFPD, % | Component B, identity | Component B, % | Conversion, % | Mono-Cl, % | 4-Cl, % |
|---|---|---|---|---|---|---|
| 16 | 0.29 | PNCC | 0.02 | 75 | 97 | 66 |
| 17 | 0.34 | DBT | 0.1 | 93 | 93 | 42.3 |
| 18 | 0.3 | FFPN | 0.02 | 80 | 99 | 57 |
| Control 3 | — | PNCC | 0.02 | 85 | 95 | 56 |

EXAMPLES 19-24

The procedure of Examples 1-5 was repeated, employing 0.02% of PNCC and various nickel, cobalt (II) and manganese (II) salts as component A. The results are given in Table IV.

TABLE IV

| Example | Component A, identity | Component A, % | Conversion, % | Mono-Cl, % | 4-Cl, % |
|---|---|---|---|---|---|
| 19 | CoPD | 1.2 | 88 | 69 | 95.5 |
| 20 | CoSt | 1.2 | 72 | 68 | 89 |
| 21 | NiPD | 1.4 | 94 | 76 | 95.6 |
| 22 | NiTMHD | 1.4 | 94 | 76 | 90.5 |
| 23 | MnSt | 1.4 | 88 | 79 | 94.8 |
| 24 | MnPD | 1.4 | 91 | 79.6 | 95 |

EXAMPLES 25-39

The procedure of Examples 1-5 was repeated, employing 0.1% of PNCC (unless otherwise noted) and in each case 1.4 wt. % of various metal salts as component A. The results are given in Table V.

TABLE V

| Example | Component A, identity | Conversion, % | Mono-Cl, % | 4-Cl, % |
|---|---|---|---|---|
| 25 | Mo(OEt)₂ | 50 | 87 | 61.5 |
| 26 | MoO₂(TMHD)₂ | 98 | 83 | 76 |
| 27 | ZrCl₄ | 6 | 61 | 58 |
| 28 | Zr(acac)4 | 95 | 95 | 74 |
| 29 | Zr(F₃acac)4 | 85 | 90 | 71 |
| 30 | TiO₂(acac)₂ | 78 | 91 | 76 |
| 31 | V(acac)₃ | 76 | 95 | 74 |
| 32 | VI₃ | 70 | 95 | 71 |
| 33 | VO(C₆H₅-acac)₂ | 65 | 97 | 72.6 |

TABLE V-continued

| Example | Component A, identity | Conversion, % | Mono-Cl, % | 4-Cl, % |
|---|---|---|---|---|
| 34 | Nb(TMHD)$_4$ | 70 | 97.6 | 71 |
| 35 | NbI$_3$ | 90 | 85 | 70 |
| 36 | Yb(acac)$_3$ | 51 | 96 | 67 |
| 37 | PdCl$_2$ | 44 | 59 | 59 |
| 38* | Pd(F$_6$acac)$_2$ | 80 | 95.5 | 74 |
| 39 | Pt(acac)$_2$ | 81 | 94.9 | 74 |

*used 0.02 wt. % PNCC

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

The invention claimed is:

1. A catalyst composition prepared by combining (A) at least one salt comprising a metal cation of a metal selected from the group consisting of a d-block Group 4-12 metal; and an organic counterion to the metal cation, derived from at least one acidic organic compound selected from the group consisting of those with an approximate pKa value relative to water of at least about 3; and (B) at least one organic sulfur compound.

2. A composition according to claim 1 further comprising chlorine and an aromatic compound.

3. A composition according to claim 2 wherein the aromatic compound is a monocyclic hydrocarbon.

4. A composition according to claim 3 wherein the aromatic compound is toluene or o-xylene.

5. A composition according to claim 1 wherein the organic compound is a carboxylic acid or a derivative thereof.

6. A composition according to claim 1 wherein the organic compound is a 2,4-dione or a derivative thereof.

7. A composition according to claim 1 wherein the metal is selected from the group consisting of copper, nickel, cobalt, manganese, molybdenum, zirconium, titanium, vanadium, niobium, palladium and platinum.

8. A composition according to claim 1 wherein component A is a copper salt.

9. A composition according to claim 1 wherein component A is a nickel salt.

10. A composition according to claim 1 wherein component A is a cobalt(II) salt.

11. A composition according to claim 1 wherein component A is a manganese(II) salt.

12. A composition according to claim 1 wherein component A is cupric acetate, cupric 2,4-pentanedionate, cupric 1,1,1,5,5,5-hexafluoro-2,4-pentanedionate, cupric benzoate, nickel acetate, nickel 2,4-pentanedionate, nickel 2,2,6,6-tetramethyl-3,5-heptanedionate, cobalt(II) acetate, cobalt(II) stearate, cobalt(II) 2,4-pentanedionate, manganese(II) acetate, manganese(II) stearate or manganese(II) 2,4-pentanedionate.

13. A composition according to claim 1 wherein component A is molybdenum oxide 1,1,1,5,5,5-hexafluoro-2,4-pentanedionate, zirconium 2,4-pentanedionate, zirconium trifluoro-2,4-pentanedionate, titanium oxide 2,4-pentanedionate, vanadium 2,4-pentanedionate, niobium 2,2,6,6-tetramethyl-3,5-heptanedionate, palladium 1,1,1,5,5,5-hexafluoro-2,4-pentanedionate or platinum 2,4-pentanedionate.

14. A composition according to claim 1 wherein component B is a dialkyl or diaryl sulfide, dialkyl or diaryl disulfide, alkyl or aryl mercaptan, phenoxathiin, thiophene, dibenzothiophene, thianthrene or phenothiazine.

15. A composition according to claim 14 wherein component B is phenothiazine-N-carbonyl chloride, N-trifluoroacetylphenothiazine, 2-chloro-N-trifluoroacetylphenothiazine or 2-trifluoromethyl-N-trifluoroacetylphenothiazine.

16. A composition according to claim 2 wherein the proportion of component A is in the range of about 0.005-10.0% by weight based on aromatic compound.

17. A composition according to claim 16 wherein the proportion of component A is in the range of about 0.07-3.0% by weight based on aromatic compound.

18. A composition according to claim 2 wherein the proportion of component B is in the range of about 0.005-10.0% by weight based on aromatic compound.

19. A composition according to claim 18 wherein the proportion of component B is in the range of about 0.01-0.1% by weight based on aromatic compound.

20. A catalyst composition for chlorinating toluene or o-xylene which comprises at least one reaction product of (A) at least one salt comprising a metal cation of a metal selected from the group consisting of a d-block Group 4-12 metal and an organic counterion derived from at least one acidic organic compound selected from the group consisting of those with an approximate pKa value relative to water of at least about 3; and (B) at least one organic sulfur compound.

21. A catalyst composition for chlorinating toluene or o-xylene which comprises (A) at least one salt of copper, nickel, cobalt or manganese with a carboxylic acid or 2,4-dione, or derivative thereof; and (B) at least one organic sulfur compound selected from the group consisting of phenothiazine-N-carbonyl chloride, N-trifluoroacetylphenothiazine, 3-chloro-N-trifluoroacetylphenothiazine and 3-trifluoromethyl-N-trifluoroacetylphenothiazine.

22. A composition according to claim 21 wherein component A is cupric acetate, cupric 2,4-pentanedionate or cupric 1,1,1,5,5,5-hexafluoro-2,4-pentanedionate.

23. A composition according to claim 21 wherein component B is phenothiazine-N-carbonyl chloride.

24. A catalyst composition for chlorinating toluene or o-xylene which comprises at least one reaction product of (A) at least one salt of copper, nickel, cobalt or manganese with a carboxylic acid or 2,4-dione, or derivative thereof; and (B) at least one organic sulfur compound selected from the group consisting of phenothiazine-N-carbonyl chloride, N-trifluoroacetylphenothiazine, 3-chloro-N-trifluoroacetylphenothiazine, and 3-trifluoromethyl-N-trifluoroacetylphenothiazine.

25. A catalyst composition prepared by combining (A) copper sulfate; and (B) at least one organic sulfur compound.

26. A catalyst composition for chlorinating toluene or o-xylene which comprises (A) copper sulfate; and (B) at least one organic sulfur compound selected from the group consisting of phenothiazine-N-carbonyl chloride, N-trifluoroacetylphenothiazine, 3-chloro-N-trifluoroacetylphenothiazine, and 3-trifluoromethyl-N-trifluoroacetylphenothiazine.

27. A composition according to claim 26 wherein component B is phenothiazine-N-carbonyl chloride.

28. A catalyst composition for chlorinating toluene or o-xylene which comprises at least one reaction product of (A) copper sulfate; and (B) at least one organic sulfur compound selected from the group consisting of phenothiazine-N-carbonyl chloride, N-trifluoroacetylphenothiazine, 3-chloro-N-trifluoroacetylphenothiazine, and 3-trifluoromethyl-N-trifluoroacetylphenothiazine.

* * * * *